(12) United States Patent
Gooi et al.

(10) Patent No.: US 10,542,883 B2
(45) Date of Patent: Jan. 28, 2020

(54) METHOD AND SYSTEM FOR LASER AUTOMATED TRABECULAR EXCISION

(71) Applicants: Patrick Gooi, Calgary (CA); Kevin Warrian, Calgary (CA)

(72) Inventors: Patrick Gooi, Calgary (CA); Kevin Warrian, Calgary (CA)

(73) Assignees: Patrick Gooi, Calgary (CA); Kevin Warrian, Calgary (CA)

( * ) Notice: Subject to any disclaimer, the term of this patent is extended or adjusted under 35 U.S.C. 154(b) by 0 days.

(21) Appl. No.: 15/752,801

(22) PCT Filed: Aug. 26, 2016

(86) PCT No.: PCT/CA2016/000219
§ 371 (c)(1),
(2) Date: Feb. 14, 2018

(87) PCT Pub. No.: WO2017/031570
PCT Pub. Date: Mar. 2, 2017

(65) Prior Publication Data
US 2018/0235462 A1  Aug. 23, 2018

Related U.S. Application Data

(60) Provisional application No. 62/210,948, filed on Aug. 27, 2015.

(51) Int. Cl.
*A61B 3/10* (2006.01)
*A61B 3/16* (2006.01)
*A61F 9/007* (2006.01)
*A61F 9/008* (2006.01)

(52) U.S. Cl.
CPC .............. *A61B 3/102* (2013.01); *A61B 3/16* (2013.01); *A61F 9/00781* (2013.01); *A61F 9/008* (2013.01)

(58) Field of Classification Search
CPC .......... A61B 3/14; A61B 3/0025; A61B 3/12; A61B 3/102; A61B 3/0058
USPC ...................................................... 351/206
See application file for complete search history.

(56) References Cited

U.S. PATENT DOCUMENTS

2013/0149734 A1* 6/2013 Ammar .............. G01N 21/6408
435/29
2014/0271780 A1* 9/2014 Hughes ................ A61K 31/381
424/428

* cited by examiner

Primary Examiner — Mohammed A Hasan
(74) Attorney, Agent, or Firm — McMillan LLP

(57) ABSTRACT

A system and method for diagnosing and treating glaucoma is presented. The system imparts pressure on the anterior chamber of a eye using a coupling mechanism, while capturing three-dimensional imagery of the eye using optical coherence tomography angiography. Applying pressure in various areas of the eye, imparts changes that can help detect parts of the eye, or diagnose certain disorders related to the drainage of aqueous humor. A controller coupled to the optical coherence tomography angiography scanner may be used to guide a laser for excision of the trabecular meshwork for enhancing aqueous humor drainage thus lowering intraocular pressure and preventing glaucoma.

18 Claims, 12 Drawing Sheets

METHOD AND SYSTEM FOR LASER AUTOMATED TRABECULAR EXCISION

PRIORITY

The application claims the benefit of the filing date of U.S. Provisional Application No. 62/210,948, filed Aug. 27, 2015, the disclosure of which is herein incorporated by reference in its entirety.

FIELD OF THE INVENTION

The present invention relates generally to medical devices. More particularly, the present invention relates to a system for diagnosing and treating glaucoma in a human eye.

BACKGROUND OF THE INVENTION

Glaucoma

Glaucoma is a disease that affects over 60 million people worldwide, or about 1-2% of the population. The disease is typically characterized by an elevation in eye pressure, known as the intraocular pressure, that causes pathological changes in the optic nerve which if left untreated can cause blindness. The increased intraocular pressure is generally caused by a resistance to drainage of aqueous humor or fluid from the eye.

Aqueous humor is a clear, colourless fluid that is continuously replenished by the ciliary body in the eye and then ultimately exits the eye through the trabecular meshwork. The trabecular meshwork extends circumferentially around the eye in the anterior chamber angle and feeds outwardly into a narrow circumferential passageway generally surrounding the exterior border of the trabecular meshwork, known as Schlemm's canal. From Schlemm's canal, aqueous humor empties into aqueous collector channels or veins positioned around, and radially extending from, Schlemm's canal. Pressure within the eye is determined by a balance between the production of aqueous humor and its exit through the trabecular meshwork.

Referring to FIG. 1, a cross-section of an eye 110 is illustrated to show the relative anatomy of Schlemm's canal 120, trabecular meshwork 130, iris 175, and anterior chamber 140. Anterior chamber 140 is bound anteriorly by cornea 180 which is connected on its periphery to sclera 185 which is a tough fibrous tissue forming the white shell of eye 110. Trabecular meshwork 130 is located on the outer periphery of anterior chamber 140 and extends 360 degrees circumferentially around anterior chamber 140 with Schlemm's canal 120 also extending 360 degrees circumferentially around the outer peripheral surface of trabecular meshwork 130.

Anterior chamber 140 of eye 110 is filled with aqueous humor which is produced by ciliary body 160 to ultimately exit eye 110 through trabecular meshwork 130. In a normal eye 110, aqueous humor passes through trabecular meshwork 130 into Schlemm's canal 120 and thereafter through a plurality of aqueous veins 170, which merge with blood-carrying veins (not shown), and into systemic venous circulation. Glaucoma is characterized by an excessive buildup of aqueous humor, which leads to an increase in intraocular pressure that is distributed relatively uniformly throughout eye 110. Resistance to flow in trabecular meshwork 130 and/or Schlemm's canal 120 can cause decreased flow of aqueous humor out of the eye 110 and increased intraocular pressure.

Treatment Methods

Treatments that reduce intraocular pressure can slow or stop progressive loss of vision associated with some forms of glaucoma and such treatments are currently the primary therapy for glaucoma. A number of treatment methods are currently used for reducing intraocular pressure to treat glaucoma including medication, laser therapies and various forms of surgery. Drug therapy includes topical ophthalmic drops or oral medications that either reduce the production or increase the outflow of aqueous humor. When medical and laser therapy fail, however, more invasive surgical therapy is typically used.

Surgical Techniques

Surgical techniques for treating glaucoma generally involve improving aqueous outflow. Trabeculectomy, a procedure which is widely practiced, involves microsurgical dissection to mechanically create a new drainage pathway for aqueous humor to drain, by removing a portion of sclera and trabecular meshwork at the drainage angle. Trabeculectomy, however, carries the risk of blockage of the surgically-created opening through scarring or other mechanisms, and has been found to have limited long-term success. Furthermore, Trabeculectomy surgery is associated with serious, potentially blinding complications.

Alternative surgical procedures to Trabeculectomy include tube shunt surgeries, non-penetrating Trabeculectomy and Viscocanalostomy. These procedures are invasive as they are "ab externo" (from the outside of the eye). Tube shunt surgeries involve significant extraocular and intraocular surgery with significant risk of surgical complications, as well as the long term risk of failure from scarring. In the case of viscocanalostomy and non-penetrating Trabeculectomy, the procedures involve making a deep incision into sclera, and creating a scleral flap to expose Schlemm's canal 120 for cannulation and dilation. Due to the delicate nature of these ab-externo approaches, they are difficult to execute. Due to the invasiveness of such procedures and the difficulty of successfully accessing the small diameter of Schlemm's canal 120 from the outside of the eye, "ab interno" techniques have been described for delivering ocular devices and compositions into Schlemm's canal 120 through trabecular meshwork 130 from the inside of eye 110.

In glaucoma, trabecular meshwork resistance creates increased intraocular pressure. Current minimally invasive glaucoma surgery (MIGS) techniques, such as iStent, Hydrus, and Trabectome, bypass trabecular meshwork 130 to reduce the intraocular pressure.

Diagnostic Systems

Optical Coherence Tomography

Tomography is a technique for displaying a representation of a cross section through a human body or other solid object using X-rays or ultrasound. Optical coherence tomography (OCT) is an established medical imaging technique that uses light to capture micrometer-resolution, three-dimensional images from within optical scattering media, such as biological tissue. OCT is based on low-coherence interferometry, typically employing near-infrared light. The use of relatively long wavelength light allows it to penetrate into the scattering medium.

Optical Coherence Tomography Angiography

Angiography is the examination by X-ray of blood or lymph vessels, carried out after introduction of a radiopaque substance. OCT Angiography (OCT-A), is the most important OCT technology developed in recent years. OCT-A detects the motion of red blood cells as intrinsic contrast, and therefore does not require the injection of extrinsic contrast dye, such as with fluorescein angiography or Indocyanine Green (ICG) angiography. This no-injection, dye-free technology is capable of three-dimensional imaging of capillary dropout or pathologic vessel growth in the leading cause of blindness: age-related macular degeneration, diabetic retinopathy, and glaucoma. The three-dimensional nature of OCT-A allows the segmentation of retinal and choroidal layers into distinct "slabs" for en face flow projection images that separately visualizes retinal and choroidal circulations, as well as abnormal choroidal neovascularization in the outer retina and retinal neovascularization in the vitreous space.

Multiple approaches for OCT-A have been developed. These include amplitude-based, phased-based, or combined amplitude/phase variance-based methods. Furthermore, new software algorithms have been developed which allow existing OCT hardware to perform OCT-A. These methods use either Doppler shift or variations in speckle pattern caused by moving red blood cells to detect both transverse and axial flow. These methods have become practical now because the high speed of Fourier-domain OCT allows multiple cross-sectional images to be obtained at the same location in very quick succession to detect relative motion in voxels contain blood flow. Both varieties of Fourier-domain OCT: spectral (a.k.a. spectral-domain or spectrometer-based) or swept-source, could be used. Three-dimensional volumetric OCT-A can be obtained in seconds. Subsequent processing allows the visualization of vascular networks down to the capillary level in both the retinal and choroidal circulations. Because of the high axial resolution of OCT, the retinal circulation could be further subdivided into the superficial and deep plexus as well as abnormal neovascularization into the vitreous space. The choroidal circulation could be subdivided into the choriocapillaris, the deeper choroid, and abnormal neovascularization above Bruch's membrane and into the retina. Anterior segment OCT-A of the episcleral space can also differentiate between aqueous veins from episcleral and conjunctival vasculature.

Laser Technologies

Types of laser of interest to eye surgery include excimer and femtosecond types of laser. An excimer laser, is a form of ultraviolet laser which is commonly used in the production of microelectronic devices, eye surgery, and micromachining. A femtosecond laser uses near-infrared wavelength light, which allows the light to be focused at a micron spot size, accurate within 5 microns in the anterior segment of the eye. Femtosecond laser has ultra short pulses ($10^{-15}$ seconds, or a femtosecond hence the name) which advantageously eliminates collateral damage of surrounding tissues, when used in eye surgery.

Known Art

U.S. Patent Publication No. 2012/0283557 A1 to Berlin, discloses a method of creating and maintaining an opening in the trabecular meshwork of a patient's eye to conduct fluid from the anterior chamber to Schlemm's canal of the eye by applying laser pulses to form at least one of a drain channel or a humor outflow opening, wherein Schlemm's canal is detected optically or by OCT.

Nakamura H, Liu Y, Witt T E, et al. Femtosecond laser photodisruption of primate trabecular meshwork: an ex vivo study. Inv Ophthal Vis Sci 2009:1198-1204, studied the use of femtosecond laser for photodisruption of the primate trabecular meshwork ex vivo using a manually operated goniolens with direct visualization.

A similar procedure to the one studied by Nakamura, but without the use of femtosecond laser, is Gonioscopy Assisted Transluminal Trabeculectomy (GATT). Gonioscopy is an eye examination of the anterior chamber between the cornea and the iris to determine whether the drainage angle is open or closed. The GATT procedure is performed via micro-incisions in the cornea. An incision about 1.0 mm in size is made in the periphery of the cornea through which the surgery is completed. After entering the eye, the surgical procedure involves cutting through trabecular meshwork 130, cannulating Schlemm's canal 120 in 360 degrees, and unroofing Schlemm's canal 120. GATT reduces intraocular pressure by restoring the trabeculo-canalicular outflow pathway. GATT increases the flow of aqueous humor from the anterior chamber, directly into and around Schlemm's canal, and out through the collector channels. GATT achieves mean post-op intraocular pressure of 15.7 mmHg at 12 months in humans. However, GATT has a steep learning curve and sometimes it is not possible to thread the full 360 degrees of Schlemm's canal, which impedes its adoption by cataract surgeons and even many fellowship trained glaucoma surgeons.

TRAB360 is a similar surgical procedure to GATT. The TRAB360 surgical instrument is a "trabeculotome"; a non-powered instrument intended for the manual cutting of trabecular meshwork 130. TRAB360 can be used to mechanically cut up to 360 degrees of trabecular meshwork 130.

Selective Laser Trabeculoplasty (SLT), is a form of laser surgery that is used to lower intraocular pressure in glaucoma. Laser energy is applied to the drainage tissue in the eye. This starts a chemical and biological change in the tissue that results in better drainage of fluid through the drain and out of the eye. This eventually results in lowering of intraocular pressure. It may take 1-3 months for the results to appear.

It is an object of this invention to provide a novel system for the diagnosis and treatment of glaucoma by reducing intraocular pressure.

SUMMARY OF THE INVENTION

According to one aspect of the invention, there is provided a system for diagnosing glaucoma, in a human eye, the system comprising a coupling mechanism adapted for imparting pressure on an anterior region of said human eye; and an Optical Coherence Tomography Angiography (OCT-A) scanner producing three-dimensional imagery of regions of said human eye while said pressure is being imparted on said anterior region of said human eye by said coupling mechanism. According to one embodiment of the invention, the coupling mechanism comprises a corneal portion and an episcleral portion. In one embodiment, the corneal portion may comprise at least one corneal central piston and at least one corneal side piston. The episcleral portion comprises at least one piston. In another embodiment, the corneal portion comprises at least one corneal central fluid jet, and at least one corneal side jet, for imparting pressure or suction on a corneal central part, and a corneal side part, respectively, of the anterior region of the human eye. In yet another embodiment, the episcleral portion comprises at least one episcleral fluid jet, for imparting pressure or suction on a scleral part of the interior region of the human eye. According to another embodiment of the invention, the system further comprises a rotatable mirror for reflecting imagery for various portions for said human eye, into the OCT-A scanner. According to another embodiment of the invention the system further comprises one or more goniolenses formed on at least one of the corneal central piston and the corneal side piston.

According to another aspect of the invention there is provided a method of identifying portions of a human eye, comprising imparting varying pressure on one of: a central cornea, a side cornea, and a sclera of said human eye using a coupling mechanism; and monitoring imagery produced by an OCT-A scanner and observing the flow of red blood cells in and out of Schlemm's canal, for identifying the location of Schlemm's canal and the trabecular meshwork of said human eye.

According to yet another aspect of this invention, there is provided a system for treating glaucoma, in a human eye, the system comprising a coupling mechanism adapted for imparting pressure on the anterior region of said human eye; an OCT-A scanner producing three-dimensional imagery of regions of said human eye while said pressure is being imparted on said anterior region of said eye by said coupling mechanism; and a laser system for excising regions of said human eye based on said three-dimensional imagery. In one embodiment, the system further comprises a computer for processing imagery produced by said OCT-A scanner and identifying parts of said human eye. In another embodiment the system further comprises a controller for directing the laser system to the regions of the human eye.

According to yet another aspect of the present invention, there is provided A method of treating glaucoma, in a human eye, comprising imparting varying pressure on one of: a central cornea, a side cornea, and a sclera of said human eye using a coupling mechanism; monitoring imagery produced by an OCT-A scanner and observing the flow of red blood cells in and out of Schlemm's canal, for identifying the location of Schlemm's canal and trabecular meshwork of said human eye; and excising at least a portion of said trabecular meshwork using a laser based on said monitoring, for producing a channel for proper drainage of aqueous humor from said human eye.

BRIEF DESCRIPTION OF THE DRAWINGS

A glaucoma system, hereinafter referred to as the Laser Assisted Transluminal Trabecular Excision (LATTE) system, is provided. Embodiments of the LATTE system will now be described, by way of example only, with reference to the attached figures, wherein:

FIG. 9C is a pictorial view of a pressurize garment for a lower human body, used to elevate the episcleral venous pressure in the human eye of FIG. 1, in accordance with an embodiment of the present invention;

DETAILED DESCRIPTION OF THE EMBODIMENTS

Figure 1:
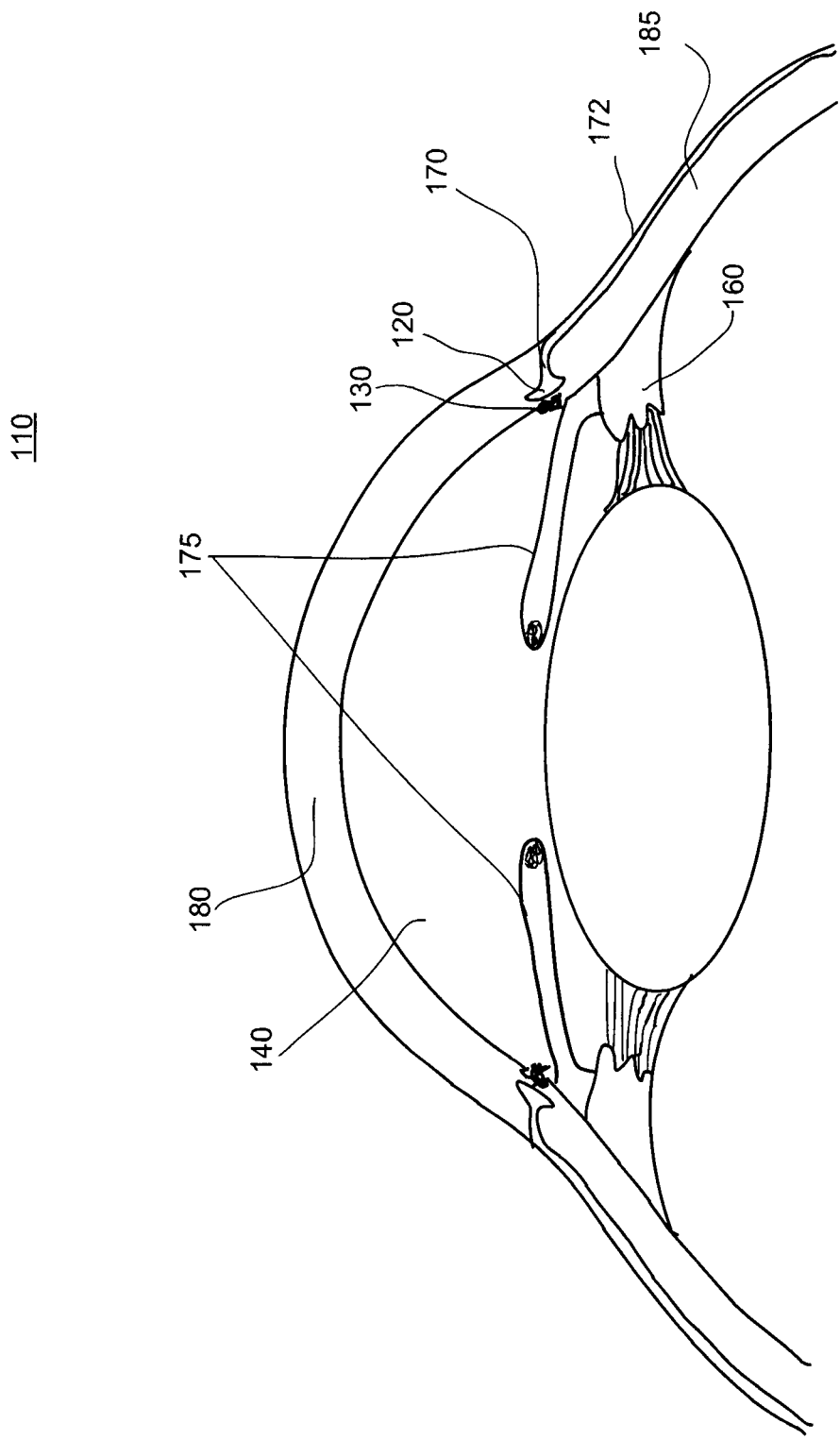
FIG. 1 is a cross-sectional view of a human eye.

While the Background of Invention described above has identified particular problems known in the prior art, the present invention provides, in part, a new and useful system and method for diagnosing and treating glaucoma. The glaucoma system provided is referred to as the LATTE system.

By applying pressure at various parts of the eye, and measuring the episcleral venous pressure, the LATTE system may help distinguish between different types of glaucoma; including, those where resistance is primarily at trabecular meshwork 130, and others where the resistance is primarily is in the post-trabecular outflow system (for example, ones with high episcleral venous pressure). Methods to investigate the degree and relative contributions of resistance at varying levels of outflow pathway (trabecular, post trabecular, and episcleral venous pressure) include but are not limited to: examining flow/change in flow for a given intraocular pressure exerted on the cornea; examining flow or change in flow as the intraocular pressure is increased; and examining flow or change in flow as the intraocular pressure and the episcleral venous pressure are varied. Examining flow or change in flow refers to examining flow through either the entire outflow pathway for aqueous humor, or focusing the analysis to a certain section such as Schlemm's canal 120, the aqueous veins 170, or the episcleral veins 172.

The LATTE system described herein uses OCT-A while simultaneously exerting dynamic changes in pressure in the different compartments of the eye, namely anterior chamber 140 and sclera 185, to create "Dynamic OCT-A", which is a non-invasive diagnostic tool that can be used to assess ocular disease across all fluid-filled networks of the eye. The LATTE system is useful in the diagnosis of, but is not limited to, glaucoma, as well as diseases of the retina, optic nerve and choroid. When assessing patients with glaucoma the LATTE system can determine whether the patient has open-angle or angle-closure glaucoma. For those with open angle glaucoma, the LATTE system can analyze the varying contributions of pre-trabecular and post-trabecular resistance.

Using a coupling mechanism which is a component of the LATTE system, the intraocular pressure, and the episcleral venous pressure are fluctuated in a controlled manner, cycling back and forth. As a result, red blood cells are refluxed into and out of Schlemm's canal 120, which can be monitored via an OCT-A camera and shown by an OCT-A scanner. Thus OCT-A is able to identify the red blood cells entering and leaving Schlemm's canal 120, and accordingly provides the capability to accurately identify the profile and location of Schlemm's canal 120.

Using the dynamic OCT-A technique presented, it is possible to identify patients that would be better served with a procedure that bypass resistance of trabecular meshwork 130, such as iStent, Trabectome, Hydrus, GATT, or TRAB360, versus patients that would be better served with a procedure that abandons conventional outflow and creates a new drainage path such as Aquesys, Trabeculectomy, tube shunt procedure, iStent Supra, Cypass, or Solx Goldshunt.

The inventors contemplate using dynamic OCT-A to assess diseases of ocular blood flow affecting the choroid, retina and optic nerve such as: Venous stasis syndrome, and ocular ischemic syndrome, by examining how blood flow of the retinal vasculature and optic nerve head changes as the intraocular pressure is varied.

A LATTE system diagnoses different types of glaucoma in a novel way known as Dynamic OCT-A. The LATTE system has a diagnostic function including the identification of Schlemm's canal 120 and trabecular meshwork 130, using anterior segment OCT-A. Accurate identification of Schlemm's canal 120 and trabecular meshwork 130, is important to correctly target a treatment laser for trabecular meshwork 130 excision, in order to perform an effective and safe procedure. As indicated earlier, the flow of aqueous humor is from the inside of eye 110 in anterior chamber 140, through trabecular meshwork 130, into Schlemm's canal 120, through collector channels, into the aqueous veins 170, and into the episcleral venous plexus. The techniques described herein use multiple methods to identify Schlemm's canal 120 using OCT-A.

The LATTE system uses a novel application of OCT-A in either spectral domain or swept source configurations, to dynamically image the fluid filled channels in the eye including, but not limited to: Schlemm's canal 120, aqueous veins 170, episcleral veins 172, episcleral arteries, retinal vasculature (arteries, veins, and capillaries), choroidal vascular, and/or optic nerve blood flow. One embodiment of the LATTE system includes the use of specialized tracers, such as dyes, molecules, or cells, or other additives. The specialized tracers are injected in the aqueous pathway either intravenously or intraocular (for example, in the anterior chamber). The tracers assist OCT-A in tracking aqueous and blood flow through the aqueous drainage pathway, thus aiding in detecting and quantifying aqueous drainage in various areas of the aqueous drainage pathway. In doing so, areas of resistance to aqueous drainage can be identified. Areas of resistance may then be targeted for treatment by laser, or by other methods.

Figure 2:
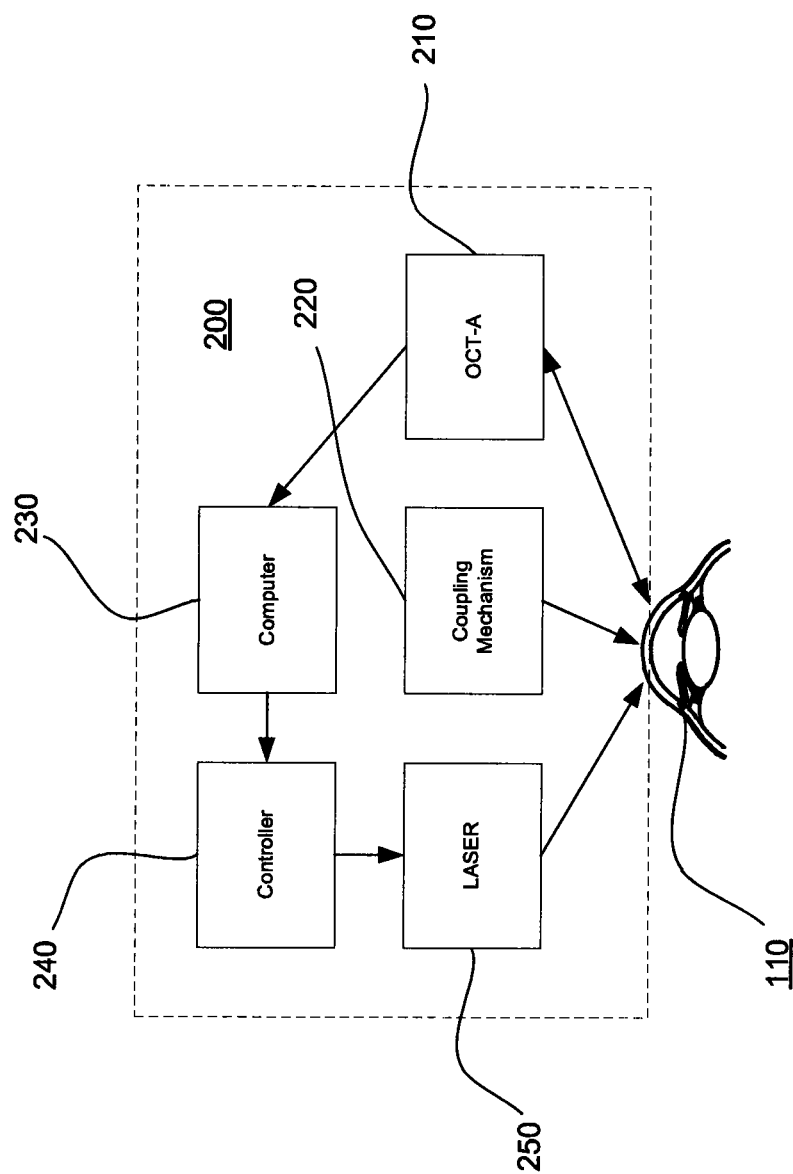
FIG. 2 is a high-level architectural diagram of a LATTE system showing its various components in relation to the human eye of FIG. 1, in accordance with an embodiment of the present invention.

FIG. 2 is a high-level architecture diagram of a LATTE system 200 showing its various components in relation to eye 110 of FIG. 1, in accordance with an embodiment of the present invention. Coupling mechanism 220 is applied to human eye 110, and is described in detail with reference to FIG. 3 to FIG. 7. OCT-A scanner 210 is directed at eye 110 for imaging the fluid filled channels in eye 110. Imaging eye 110 by OCT-A scanner 210 may be done at any time, but in some embodiments imaging is done while pressure and/or suction are applied to parts of eye 110 using coupling mechanism 220 as detailed below. OCT-A scanner 210 comprises an OCT-A camera, and other hardware for capturing three-dimensional images of parts of eye 110. Computer 230 is operatively connected to OCT-A scanner 210 for capturing images produced by OCT-A and processing such images. Images captured using OCT-A scanner 210 appear on a monitor screen operatively connected to computer 230. In some embodiments computer 230 and the monitor screen operatively connected thereto are integral parts of OCT-A scanner 210. In other embodiments computer 230 is a separate entity that is operatively connected to OCT-A scanner 210. When using LATTE system 200 for diagnostic purposes, an ophthalmologist/surgeon monitors the imagery and can make diagnostic assessments. In this case no other components of LATTE system 200 are necessary.

When using LATTE system 200 for surgical purposes, controller 240 is operatively connected to computer 230. Computer 230 may run image recognition software which identifies the location of various parts of eye 110. Computer 230 may provide information to controller 240 regarding the location of certain parts of the eye that need a surgical procedure applied thereto. For example, the image recognition software may indicate the location of trabecular meshwork 130 to controller 240. Controller 240 is operatively connected to laser 250 and maybe used to control the operation thereof. For example, controller 240 may comprise a robotic arm on which laser 250 is mounted and controller 240 may direct laser 250 towards the precise location of trabecular meshwork 130 for laser excision. Laser 250 maybe an excimer laser, or a femtosecond laser, described earlier.

Figure 3:
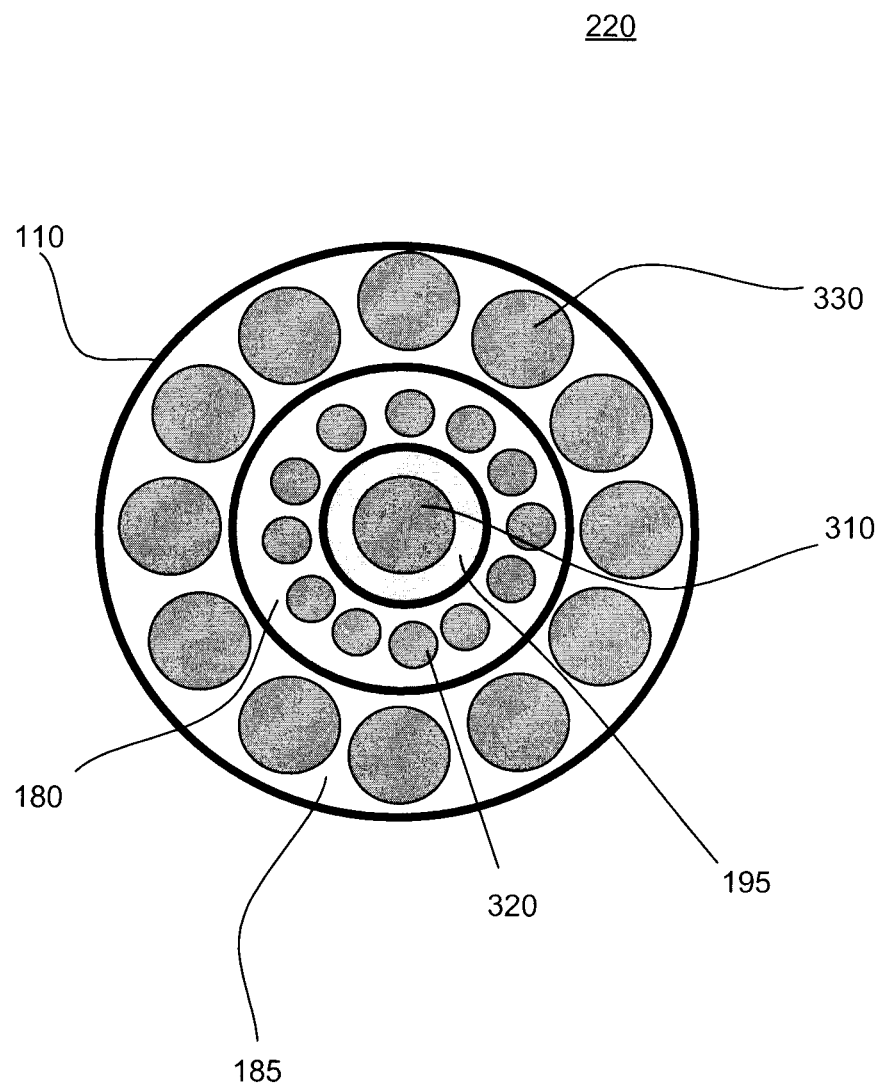
FIG. 3 is a top plan view of a coupling mechanism featuring a corneal central piston, corneal side pistons, and episcleral pistons, coupled to the human eye of FIG. 1, in accordance with an embodiment of the present invention.

FIG. 3 is a top plan view of coupling mechanism 220, in relation to human eye 110, in accordance with an embodiment of the present invention. Coupling mechanism 220 engages the anterior segment of eye 110. Coupling mechanism 220 is divided into two main components: a corneal portion, and an episcleral portion. The corneal portion covers cornea 180, and is further subdivided into a corneal central piston 310, and one or more corneal side pistons 320. In an embodiment shown in FIG. 3, the corneal side portion comprises a plurality of corneal side pistons 320 which circumferentially surround corneal central piston 310. Corneal central piston 310 covers the central part of cornea 180, which generally corresponds to eye pupil 195. Corneal side pistons 320 cover the off-center part of cornea 180 generally above, and substantially in alignment with iris 175. The episcleral portion comprises a plurality of episcleral pistons 330, which cover at least a portion of sclera 185.

Figure 4:
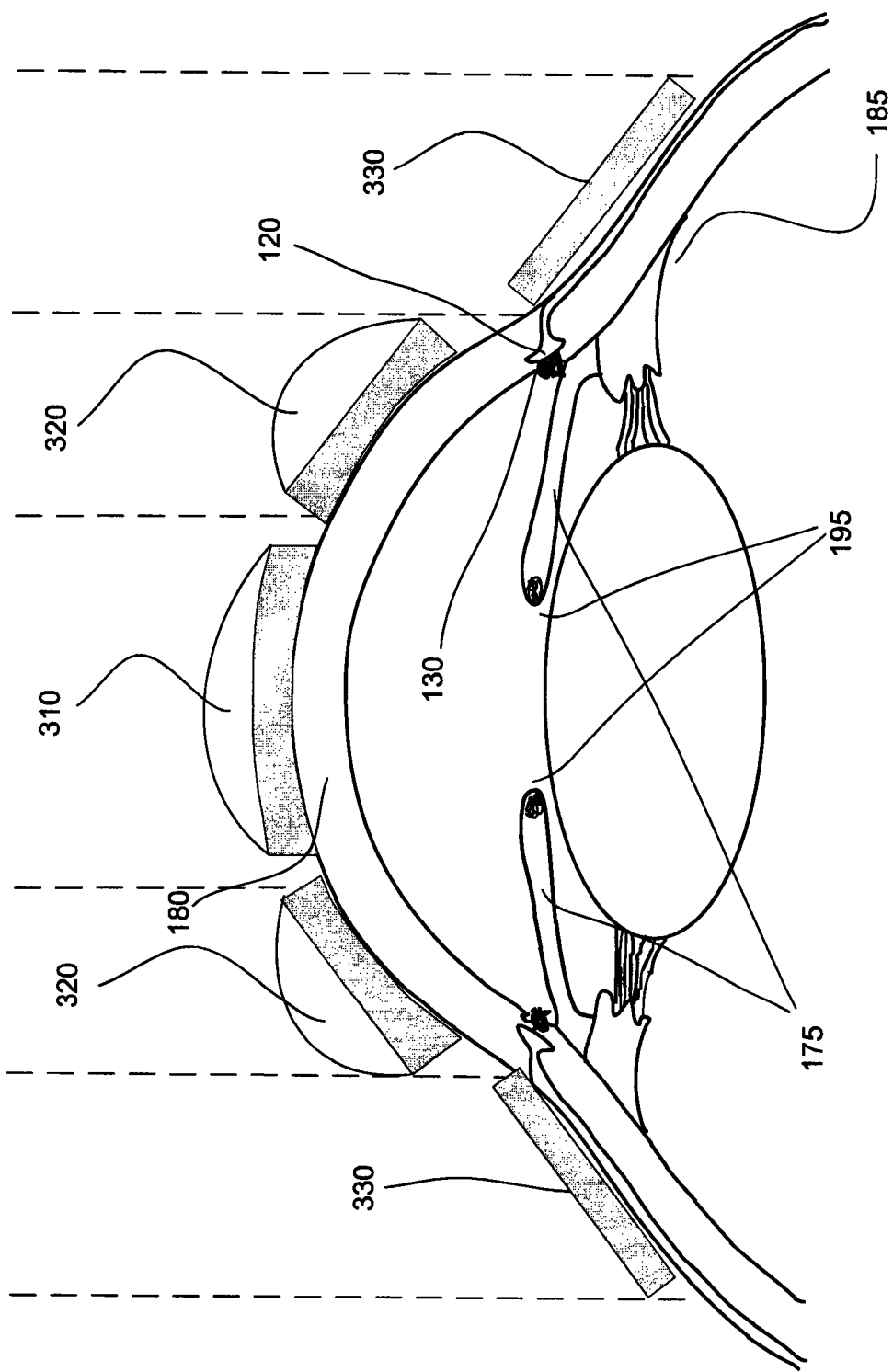
FIG. 4 is a cross-sectional view of the coupling mechanism of FIG. 3, coupled to the human eye of FIG. 1, in accordance with an embodiment of the present invention.

FIG. 4 is a cross-sectional view of coupling mechanism 220, featuring corneal central piston 310, corneal side pistons 320, and episcleral pistons 330, in relation to human eye 110, in accordance with an embodiment of the present invention. Corneal central piston 310, corneal side piston 320, and episcleral piston 330, are preferably made from special material and designed to negate the optical effects of cornea 180. In this embodiment each of corneal pistons 310 and 320 may have a goniolens built therein, and may be made of special optical material which is transparent for easy viewing of the internals of eye 110 therethrough. Corneal pistons 310, and 320 are shown with Keoppe direct goniolenses which are curved to eliminate total internal reflection. Other types of lenses such as Goldmann indirect goniolenses which utilize mirrors, and Zeiss indirect goniolenses which employ prisms, may also be built into corneal pistons 310 and 320. Episcleral pistons 330, are inclined, and maybe curved, to engage sclera 185. In another embodiment (not shown) episcleral pistons 330 may also employ goniolenses built therein. In an alternate embodiment, the episcleral portion may comprise a single piston (not shown) shaped as a truncated cone, circumferentially surrounding the corneal side portion, and having sidewalls adapted to engage sclera 185. In another embodiment the corneal side portion may comprise a single piston (not shown) shaped as a truncated cone, circumferentially surrounding the corneal central piston 310, and having sidewalls adapted to engage the side part of cornea 180.

Figure 5:
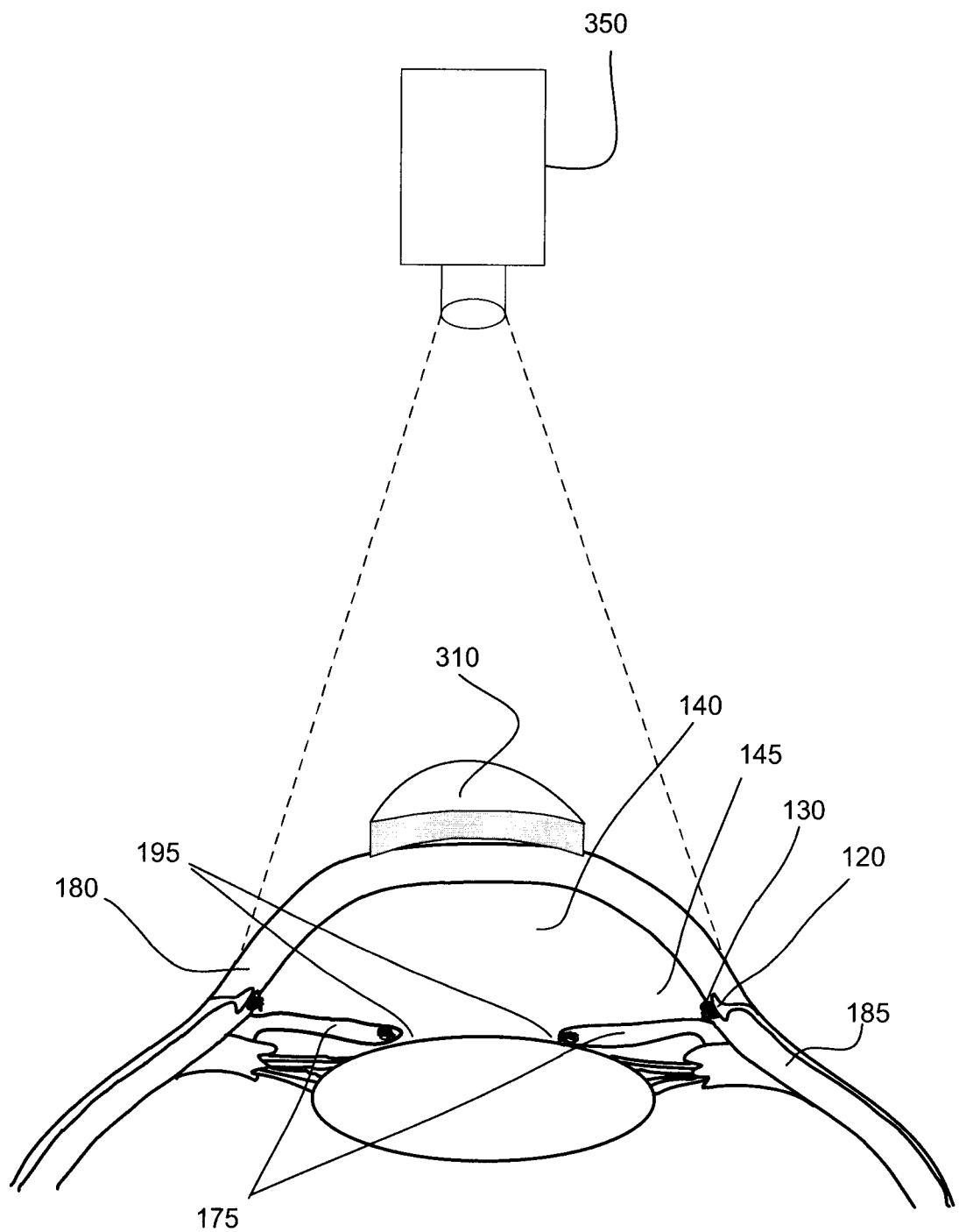
FIG. 5 is a cross sectional view of the corneal central piston of the coupling mechanism of FIG. 3, applied to the corneal central part of the human eye of FIG. 1, in accordance with an embodiment of the present invention.

A diagnostic use of the LATTE system, in accordance with an embodiment of the present invention, is presented with reference to FIG. 5. FIG. 5 is a cross sectional view of corneal central piston 310 of coupling mechanism 220, applied to the corneal central part of human eye 110, with OCT-A camera 350 in use. In this embodiment corneal central piston 310 engages the central part of cornea 180, substantially in alignment with eye pupil 195, and exerts pressure in this area. When pressure is exerted in the central part of cornea 180, the pressure opens anterior chamber angle 145, in a manner similar to that which takes place when using dynamic gonioscopy where pressure is applied using a Sussman gonioprism as is known in the art. Opening up the anterior chamber angle 145 gives a better view of the trabecular meshwork 130. Opening up chamber angle 145 is also useful for patients which suffer from both closed-angle glaucoma and trabecular meshwork 130 drainage problems. For such patients the angle needs to be opened during surgery for access to trabecular meshwork 130 for treating drainage problems by laser excision (not shown).

Figure 6:
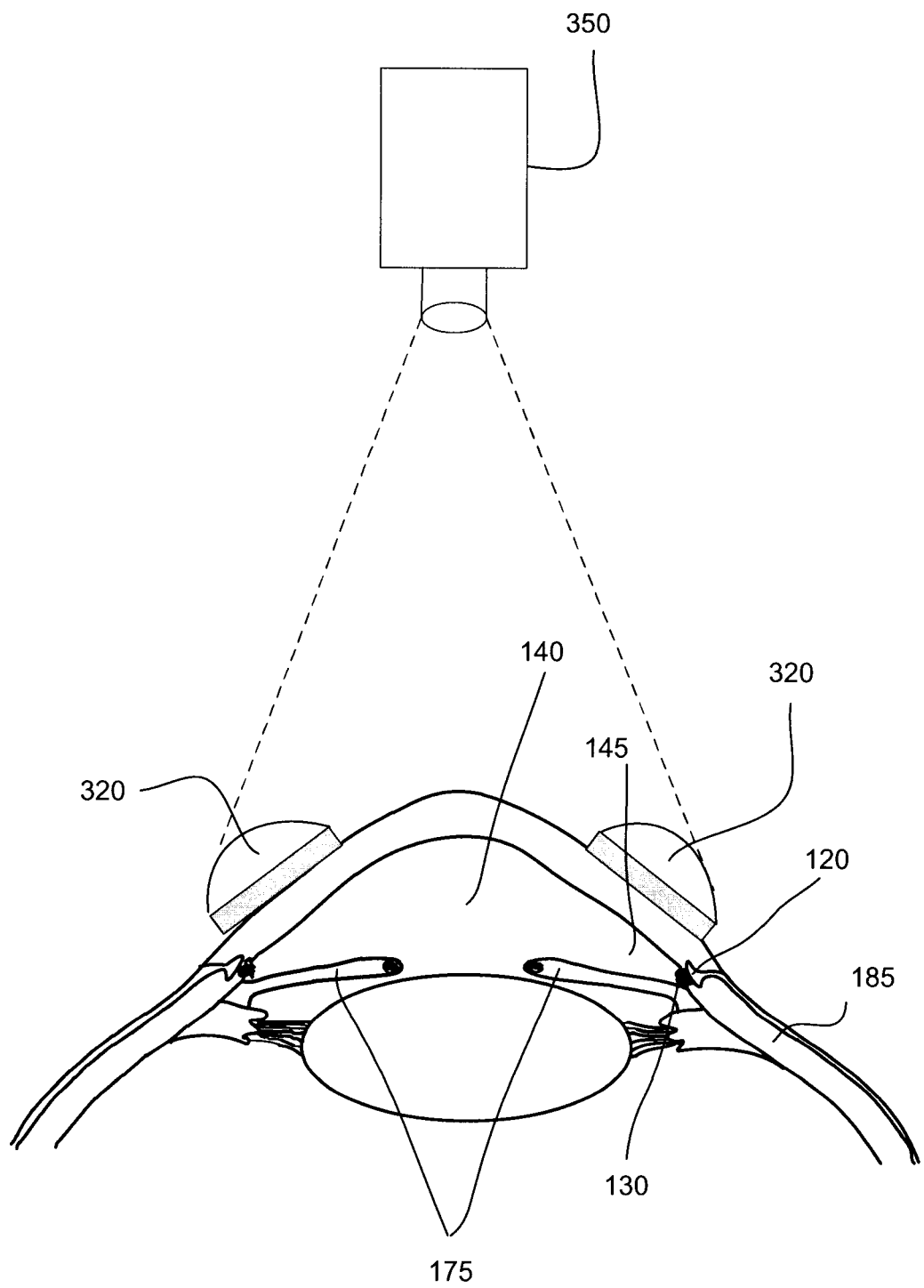
FIG. 6 is a cross sectional view of the corneal side pistons of the coupling mechanism of FIG. 3, applied to the corneal side part of the human eye of FIG. 1, in accordance with an embodiment of the present invention.

A diagnostic use of the LATTE system, in accordance with another embodiment of the present invention, is presented with reference to FIG. 6. FIG. 6 is a cross sectional view of corneal side pistons 320 of coupling mechanism 220, applied to the corneal side part of human eye 110, with OCT-A camera 350 in use. Corneal side pistons 320 cover the side part of cornea 180. When pressure is exerted in the side part of cornea 180, the pressure causes anterior chamber angle 145 to close, in a manner similar to that which takes place when using gonioscopy where pressure is applied with a Goldman-type gonioprism, as is known in the art. This is used to stress-test eye 110 for susceptibility to closed-angle glaucoma. By noting the force that needs to be applied to the side part of cornea 180, patients with risk for closed-angle glaucoma can be identified. Specifically if it takes less force than it normally would to close anterior chamber angle 145 in a patient, then that patient is at a risk for closed-angle glaucoma.

Figure 7:
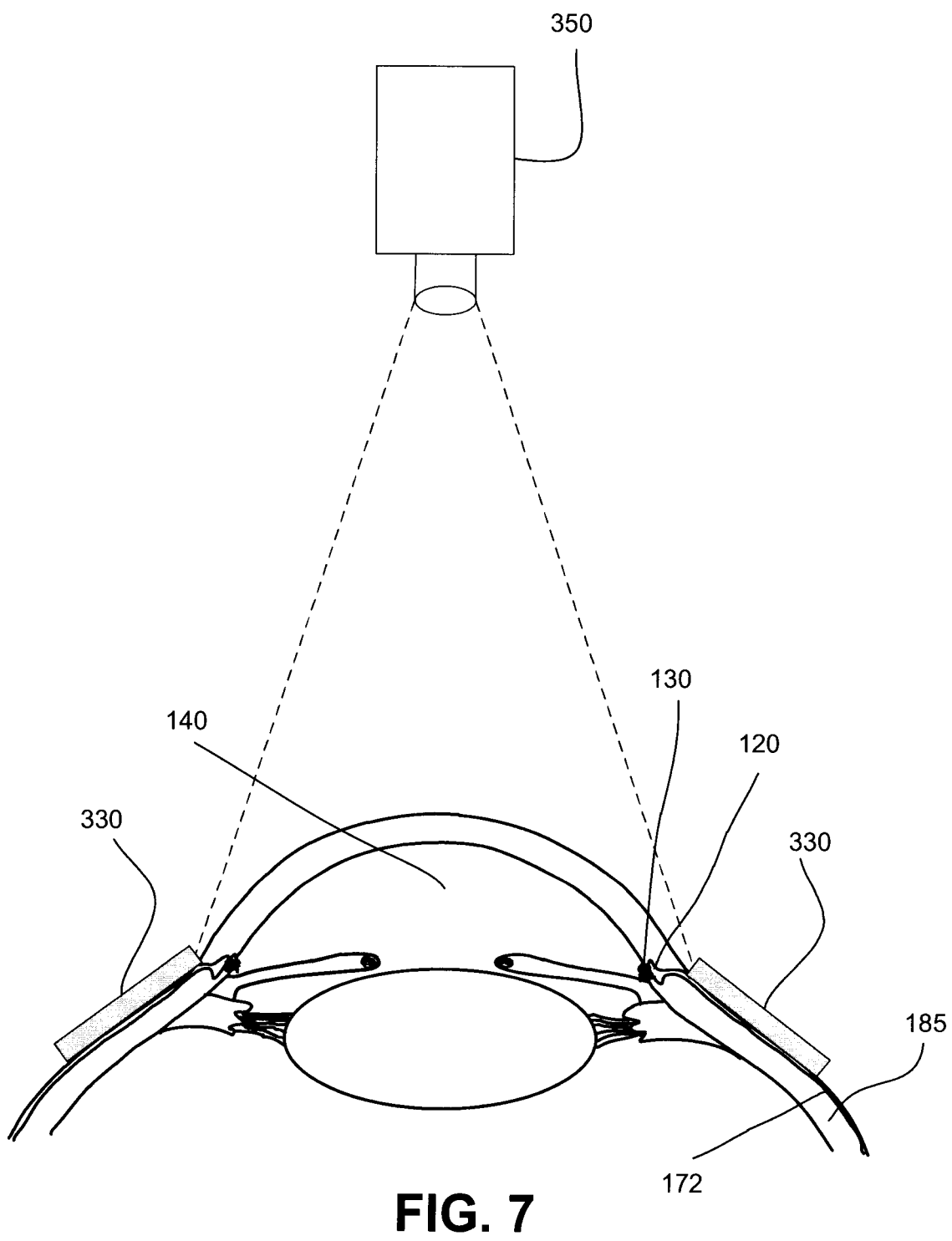
FIG. 7 is a cross sectional view of the episcleral pistons of the coupling mechanism of FIG. 3, applied to the episcleral part of the human eye of FIG. 1, in accordance with an embodiment of the present invention.

A diagnostic/surgical use of the LATTE system, in accordance with yet another embodiment of the present invention, is presented with reference to FIG. 7. FIG. 7 is a cross sectional view of the episcleral pistons 330 of coupling mechanism 220, applied to the episcleral part of human eye 110, with OCT-A camera 350 in use. Through application of pressure and/or vacuum to sclera 185, episcleral venous pressure is either increased or decreased. For example, by applying pressure to sclera 185 using episcleral pistons the episcleral venous pressure increases causing aqueous humor to reflux back into the anterior chamber 140, via Schlemm's Canal 120, and the trabecular meshwork 130. However, given the semi-porous nature and resistivity of the trabecular meshwork 130, aqueous humor accumulates in Schlemm's canal 120. This cause Schlemm's canal 120, to distend making it easy to view and identify, as well as easy for targeting by a laser for excision. Another use for this embodiment is to determine whether there is any constriction of blood flow downstream of the episcleral veins 172. For example, pressure may be applied to the sclera 185 and the closure of the episcleral vein 172 may be monitored. The pressure required to close episcleral veins 172 will vary depending on the presence of constriction of blood flow downstream of episcleral veins 172, such as neck veins.

Figure 8:
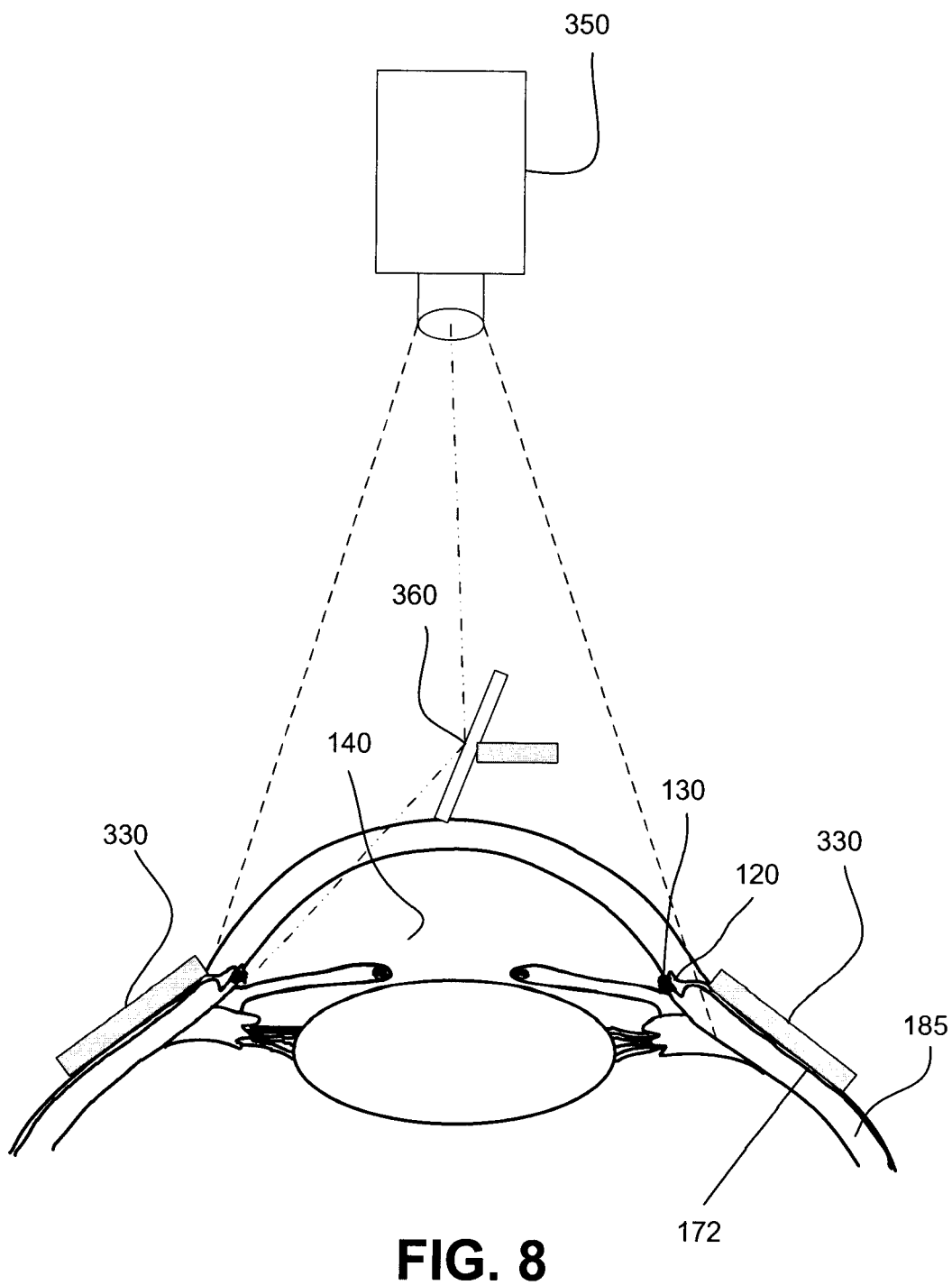
FIG. 8 is a cross sectional view of the episcleral pistons of the coupling mechanism of FIG. 3, applied to the episcleral part of the human eye of FIG. 1, in accordance with another embodiment of the present invention.

FIG. 8 is similar to FIG. 7 but includes rotatable mirror 360. A similar arrangement may also be used with corneal central piston 310 and corneal side piston 320, however they are not shown for brevity. In operation, rotatable mirror 360 is rotated to reflect different regions of eye 110 to OCT-A for capture by camera 350. Rotatable mirror 360 may be rotated manually, or automatically by means of motor (not shown) or any other suitable mechanism. Rotatable mirror 360 may be formed integrally with coupling mechanism 220, or be a separate device. In another embodiment a rotatable lens (not shown) may be used. The rotatable lens may be formed integrally with coupling mechanism 220, or be a separate device.

For the above-described embodiments, pressure applied by any one of corneal central piston 310, corneal side piston 320, and episcleral piston 330 may vary. In some embodiments the pressure is constant and steady. In other embodiments the pressure may be gradual. In other embodiments, the pressure may be intermittent being applied multiple times per minutes, or even multiple times per second. The pressure applied by the pistons is preferably provided by automated means. Such automated means would be apparent to those skilled in the art. For example, pistons 310, 320, or 330 may be actuated via hydraulic means, or by means of electromagnets, relays, or the like. Actuating mechanisms for the pistons would preferably have means of varying and measuring pressure being applied by the pistons to eye 110.

In an alternate embodiment, the LATTE system may impart a force on the various parts of human eye 110, such as cornea 180 and the episclera, in a non-contact method using targeted jets of air or other biologically compatible fluid. The targeted jets of fluids may be also divided into: a corneal central jet, one or more corneal side jets, and episcleral jets. The jets may be configured to impart vacuum forces in addition to pressure forces. Pressure applied to the eye by either the pistons or the jets may be steady, constant pressure, or it may be intermittent pressure applied multiple times per minute or multiple times per second, or a combination thereof. A combination of both pistons and jets may also be used. For example, jets in suction mode may be applied to the episclera, while pressure using pistons may be applied to cornea 180.

Figure 9A:
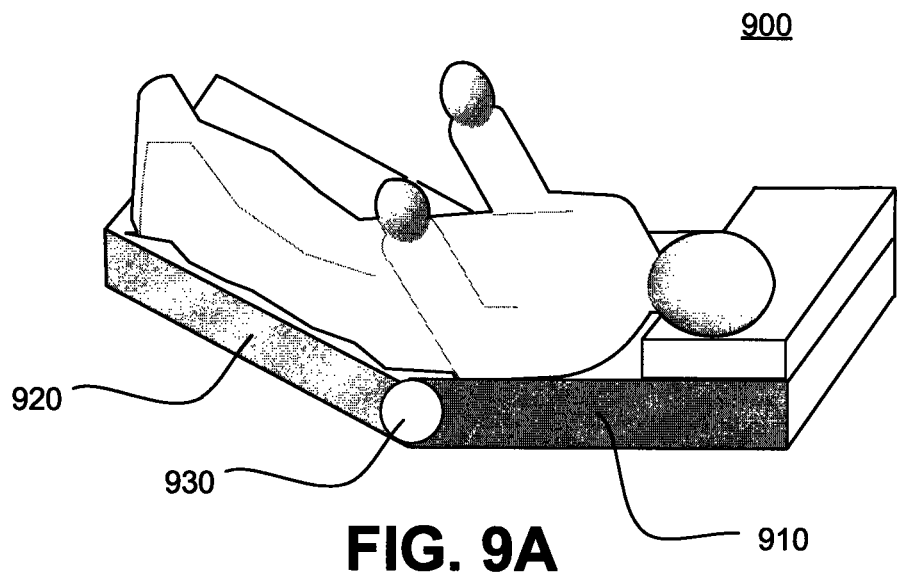
FIG. 9A is a pictorial view of a bed with a reclining lower portion used to elevate the episcleral venous pressure in the human eye of FIG. 1, in accordance with an embodiment of the present invention.
Figure 9B:
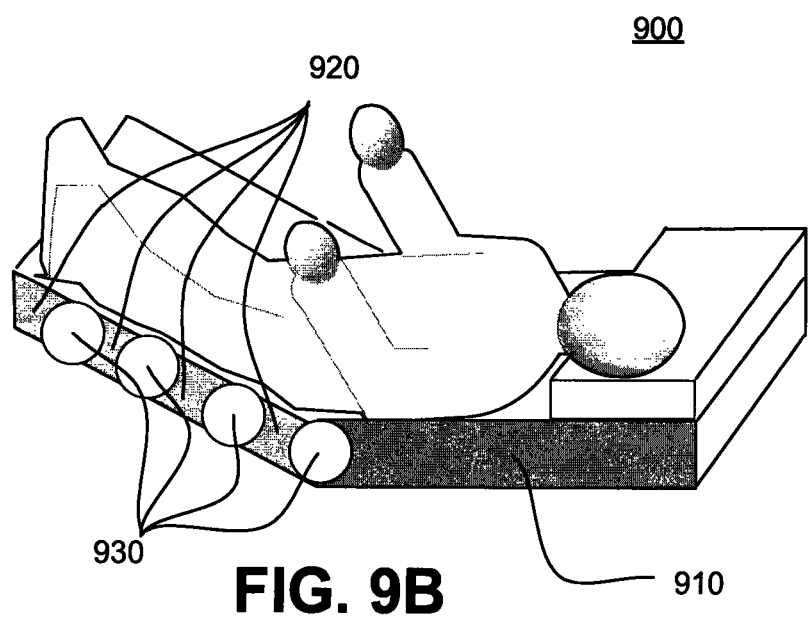
FIG. 9B is a pictorial view of a bed with a reclining lower portion used to elevate the episcleral venous pressure in the human eye of FIG. 1, in accordance with another embodiment of the present invention.
Figure 9C:
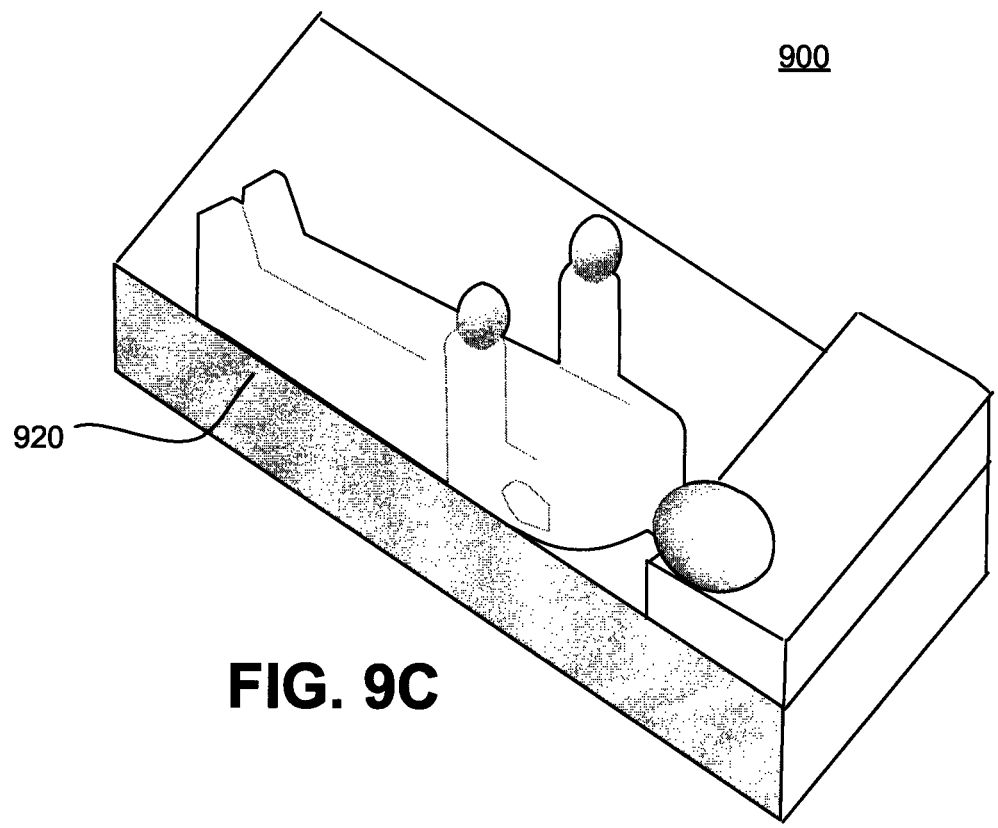
FIG. 9C is a pictorial view of a reclining bed used to elevate the episcleral venous pressure in the human eye of FIG. 1, in accordance with yet another embodiment of the present invention.

As mentioned earlier, elevating the episcleral venous pressure causes Schelmm's canal 130 to distend making it easy to identify using OCT-A. In addition to using the coupling mechanism 220, and specifically episcleral pistons 320 as presented earlier, to elevate the episcleral venous pressure other methods and devices are also provided. For example a bed 900 with a straight lower-body portion 920 reclining about a pivot point 930 is shown in FIG. 9A. In another embodiment, bed 900 with a reclining lower-body portion comprised of multiple sections 920 reclining about multiple pivot points 930 is shown in FIG. 9B. In yet another embodiment, entire bed 900 is reclining as shown in FIG. 9C. In all embodiments shown in FIG. 9A to FIG. 9C, as a patient lies in bed in a supine position and rests their lower body on the declining portion, some blood rushes towards the patient's head causing an elevation in the episcleral venous pressure thus causing Schlemm's canal 130 to distend.

Figure 9D:
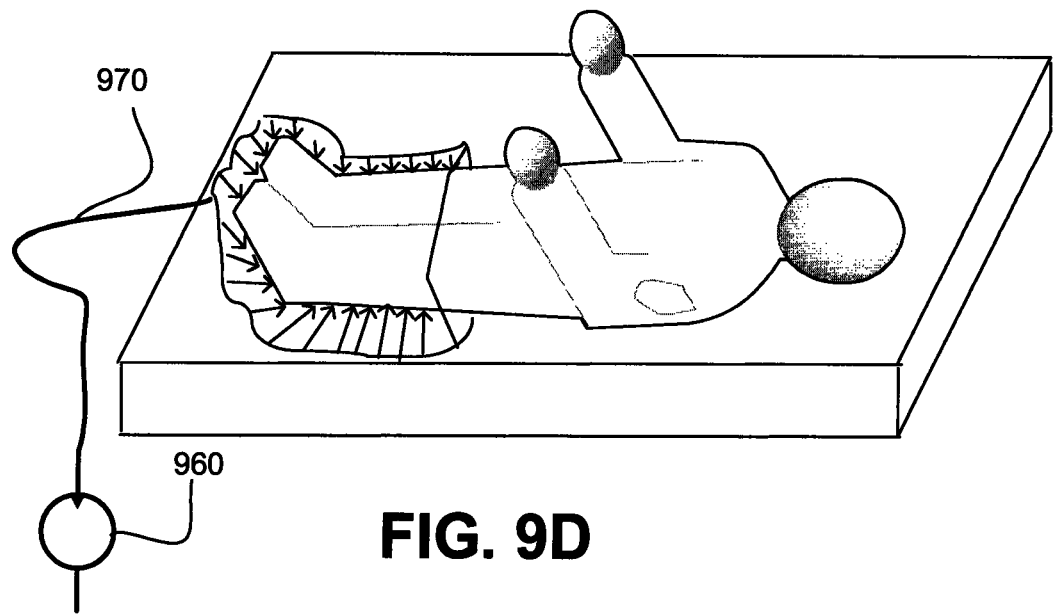

In another embodiment a patient's episcleral venous pressure is elevated by means of a pressurized garment. As shown in FIG. 9D, a patient's lower body is wrapped or inserted in garment 950 that can exert pressure on the patient's lower body. In this embodiment garment 950 may be an inflatable bag-like structure similar to blood pressure cuffs known in the art. Garment 950 is pressurized by means of pumping air therein using pump 960 and via hose 970. In another embodiment garment 950 may be made of highly elastic material. Pressure exerted on the patient's lower body causes some blood to rush towards the patient's head increasing the episcleral venous pressure and causing Schlemm's canal 130 to distend.

A LATTE system provides for treating glaucoma as effectively as incisional surgery but with minimal risks. LATTE has a safety profile that is the same as those of non-surgical treatments. A LATTE procedure may be performed in a clinic, not necessarily in the operating room, on patients with glaucoma of virtually any stage. A LATTE procedure can be performed earlier in the glaucoma treatment paradigm; prior to glaucoma incisional surgery.

Figure 10:
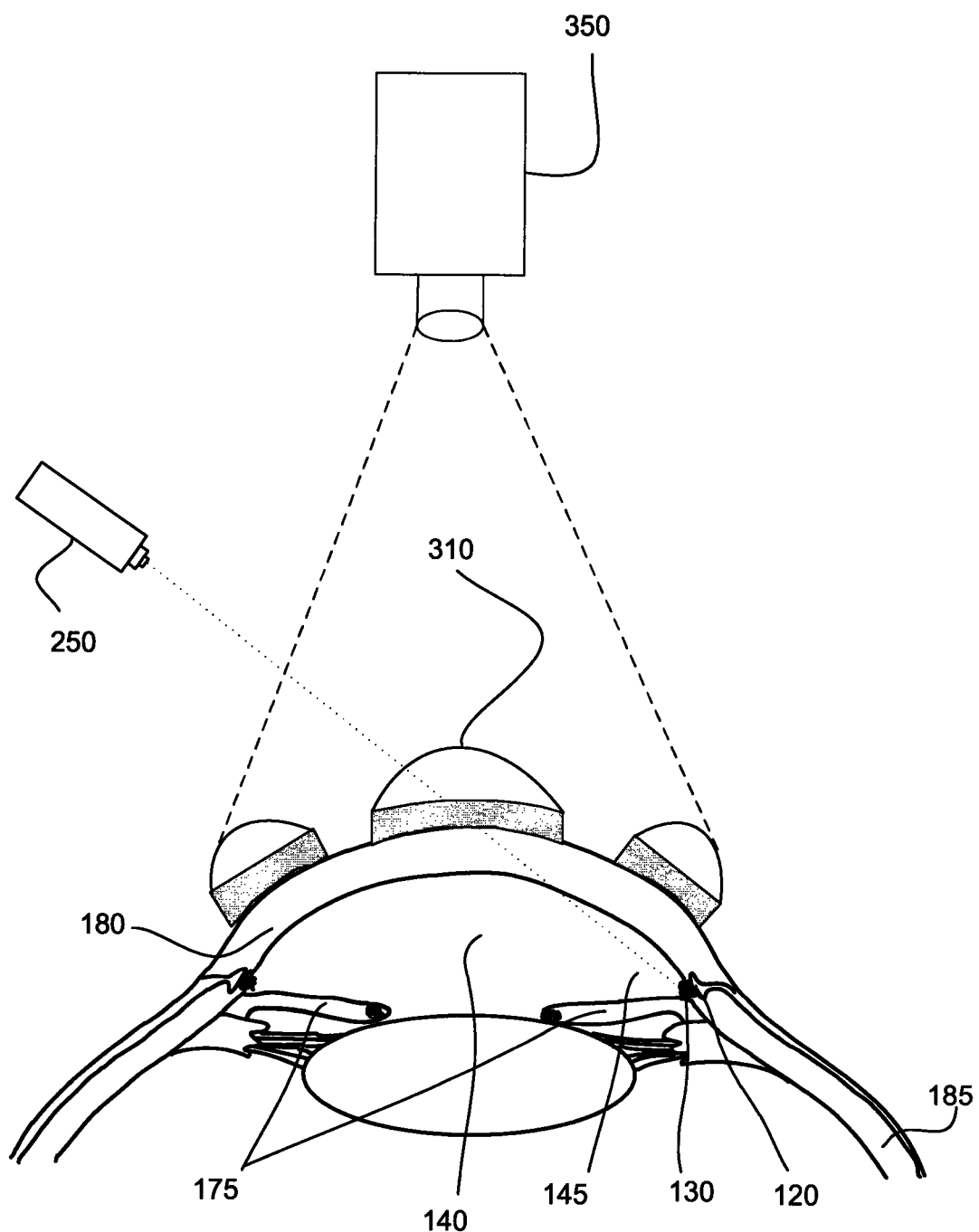
FIG. 10 depicts a trabecular meshwork excision procedure using the LATTE system, in accordance with an embodiment of the present invention.
Figure 11:
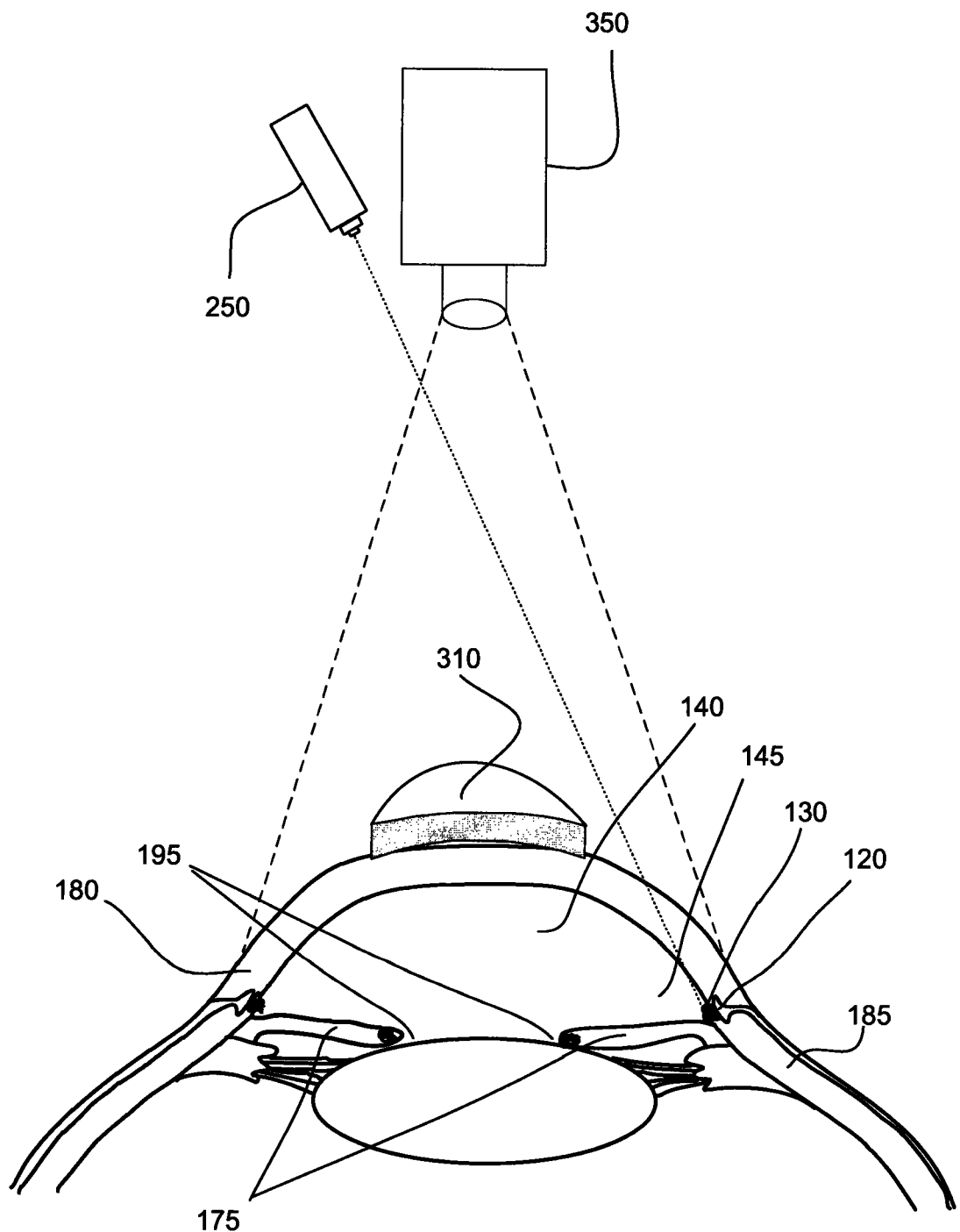
FIG. 11 depicts a trabecular meshwork excision procedure using the LATTE system, in accordance with another embodiment of the present invention.

For treatment of a disorder, an automated femtosecond laser and/or excimer laser delivery under OCT guidance may excise the trabecular meshwork as a glaucoma treatment. FIG. 10 depicts a trabecular meshwork excision procedure using the LATTE system including coupling using corneal central piston 310, corneal side pistons 320, OCT-A using OCT-A camera 350, and trabecular meshwork excision using laser 250. Using the image guidance of angle structures from dynamic OCT-A, the system identifies the inner wall of Schlemm's canal 120 and/or the trabecular meshwork 130 for laser excision. Specifically laser 250 may be operated at a low intensity just to form a dot on the portion of eye 110 it is currently aimed at. The formed dot may be detected by image recognition software on computer 230. Knowing the current position of the laser dot, and the desired location for excision, controller 240 guides laser 250 to move in a specific direction until the laser dot coincides with the desired location for excision. Controller 240 can direct laser 250 to excise some or all 360 degrees of trabecular meshwork 130 and unroofing Schlemm's canal 120. Pressure applied by corneal central piston 310 and corneal side piston 320, prevent blood from refluxing back into the anterior chamber so OCT-A scanner 220 will always have a clear view of the area targeted for excision. Accordingly, image recognition software will always be able to detect the position of the laser and controller 240 is always able to direct the laser to complete the excision procedure at the correct areas. In the embodiment shown in FIG. 10, laser is applied through the goniolens formed integrally with corneal central piston 310. Other embodiments are contemplated. For example FIG. 11 depicts an embodiment for laser excision, wherein laser is applied directly to trabecular meshwork 130, while OCT-A uses the goniolens on central corneal piston 310 to monitor the anterior chamber 140.

Laser 250 may be an excimer laser or a femtosecond laser, and therefore it can be used to ablate or excise tissue in a precise manner without causing collateral thermal damage to adjacent structures. The procedure is aimed at unroofing the inner wall of Schlemm's canal 120 without damaging the collector channels or components of the post-trabecular outflow system. Fragments of the ablated trabecular meshwork are cleared from the eye through the collector channels and aqueous veins 170. Obliteration of the trabecular meshwork reduces resistance to outflow and intraocular pressure is thus lowered.

The system shown in FIG. 10 may also be used to diagnose blockage or constriction in trabecular meshwork 130. In this mode pressure is applied to the anterior chamber 140, using corneal central piston 310, and corneal side piston 320. The intraocular pressure is measured and compared with the pressure applied with the pistons. If trabecular meshwork 130 is constricted or blocked, less pressure by pistons 310 and 320, would be needed to elevate the intraocular pressure to a certain level.

Over time, wound healing, fibrosis and fibrous metaplasia of the endothelial lining of the trabecular meshwork may cause failure of glaucoma surgeries such as GATT, Trabectome, iStent and Hydrus implants. In particular in-growth of fibrous tissues over the opening of the collector channels to Schlemm's canal causes increased resistance to outflow that increases intraocular pressure after time and can lead to surgical failures after GATT, iStent, and Hydrus. In the setting of surgical failure due to fibrosis over the openings of the collector channels into Schlemm's canal, dynamic OCT-A can be used to reflux red blood cells from the episcleral veins, into the collector channels up to the point of the junction between the collector channels and Schlemm's canal. By observing the reflux of red blood cells, using OCT-A, any fibrosed junctions can be identified. LATTE can then target these fibrosed junctions, and excise the fibrotic tissue in a targeted manner. This restores communication between Schlemm's canal and the collector channels which reduces resistance to outflow and thereby lowers intraocular pressure. Therefore, LATTE is potentially a repeatable procedure, whereas GATT and other MIGS are not repeatable. LATTE with Dynamic OCT-A is a potentially repeatable glaucoma therapeutic option.

Dynamic OCT-A can accurately and automatically identify trabecular meshwork 130 for surgeons unfamiliar with gonioscopy. The surgeon learning curve may be much easier for LATTE, since the surgeon does not need to develop gonioscopic skills for LATTE, as the identification of Schlemm's canal 120 is performed automatically, by using pattern recognition on captured images. Computer software, on computer 230, adapted to recognize the opening to Schlemm's canal can be used to automatically identify Schlemm's canal 120. In addition, rotatable mirror 360, shown in FIG. 8, can be rotated to reflect all 360 degrees of Schlemm's canal onto OCT-A camera 350 during surgery. The rotation of mirror 360 can be controlled by software on computer 230 and/or controller 240, to show the full 360 degrees of Schelmm's canal 120 as femtosecond laser 250 excises trabecular meshwork tissue 130. Even for surgeons well-versed in gonioscopy, sometimes the lack of trabecular meshwork pigmentation results in difficulty in identifying the trabecular meshwork. Dynamic OCT-A functionally identifies Schlemm's canal and the trabecular meshwork, allowing for more accurate targeting of tissues even in the setting of low trabecular meshwork pigmentation.

As mentioned laser 250 may be either a femtosecond or an excimer laser. Femtosecond laser photodisrupts tissue, while excimer laser ablates tissue. Both work without thermal damage (unlike Trabectome), reducing the risk of post-operative inflammation, fibrosis, and surgical failure. The laser also ensures there is an open cleft of the trabecular meshwork 130 in Schlemm's canal 120, as opposed to GATT which leaves two leaflets of the trabecular meshwork 130 which could eventually fibrose and close off. Thus, the LATTE system most likely has a lower rate of surgical failure over the long-term compared to GATT or TRAB360.

The automatically rotatable mirror 360 allows full 360 degree treatment of Schlemm's canal, unlike iStent and Hydrus, which treat at most 120 degrees. In GATT, treating the full 360 degrees of Schlemm's canal is not always possible, since some sections of Schlemm's canal are narrow and fibrosed, so it is not possible to thread the probe or suture the full 360 degrees. Hence, if Schlemm's canal is not continuously patent circumferentially, GATT may not be as effective.

Excision of the trabecular meshwork by LATTE may be superior to GATT, in which leftover leaflets of the trabecular meshwork potentially heal together and cause surgical failure. Furthermore, with LATTE, the laser does not depend on a continuously circumferentially patent Schlemm's canal.

For patients with cataracts and glaucoma, LATTE is performed during femtosecond cataract surgery, or after cataract surgery in pseudophakic patients. LATTE, similar to GATT, likely does not rely on cataract extraction for lowering intraocular pressure, unlike procedures such as iStent, Trabectome, and Hydrus. In young glaucoma patients, LATTE would be performed without cataract extraction. The angled femtosecond laser could also benefit cataract surgery, as the angled laser could segment the nucleus further out toward the equator.

Advantageously, LATTE is a procedure where no corneal incisions are necessary, thereby significantly reducing the risk of endophthalmitis. This would allow LATTE to be performed in more settings, such as a laser clinic, as opposed to a sterile operating room. Therefore LATTE may be as effective as glaucoma surgical procedures but has a much better safety profile. If temporary hypotony does occur, it is preferred to have no corneal incisions so that bacteria cannot enter the eye via leaky wounds.

In LATTE, dynamic coupling, in the form of applying pressure to the cornea or sclera, while applying the femtosecond laser to the eye enables surgeons to slightly elevate intraocular pressure in the eye which can eliminate blood reflux through Schlemm's canal thus making the surgery much safer. In TRAB360, the opposite occurs since the intraocular pressure is constantly falling due to the manipulation of instruments through leaking incisions. In addition, in TRAB360, blood refluxes through Schlemm's canal and the surgeon slowly loses view. This is currently a main challenge in virtually all MIGS; it is a race against time where the surgeon wants to complete the procedure in 2 minutes before the surgeon loses view of angle structures. Once the surgeon loses view, the risk of incomplete surgery, cataract formation, iridodialysis, and/or cyclodialysis significantly increases.

LATTE may be performed under topical anesthetics or anesthetic gel, making LATTE procedures much safer than TRAB360, which usually requires a retrobulbar block, which can potentially blind and even kill the patient. LATTE is also potentially repeatable in the setting of MIGS surgical failure due to fibrosis over the junctions between Schlemm's canal and the collector channels.

The LATTE system compared to Selective laser trabeculoplasty (SLT) and TRAB360 or GATT has superior efficacy to SLT (which is effective in about 60% of cases) and has similar efficacy to GATT/TRAB360 (which is effective in around 80-90% or cases). LATTE may have even better efficacy than TRAB360, since using OCT-A to guide the laser is more accurate than gonioscopy where the targeted area such as the trabecular meshwork is viewed using a manually held gonioscope, especially in patients with low trabecular meshwork pigmentation.

Since the trabecular meshwork is completely obliterated in the area of treatment, that should reduce the risk of a post-treatment intraocular pressure spike. The LATTE system is also much safer than TRAB360, since fewer or no incisions are necessary. This would virtually eliminate the risk of endophthalmitis.

The LATTE system also presents an easier procedure for the surgeon than SLT. With anterior segment OCT, the LATTE system accurately identifies the ocular anatomy with micron resolution. This is not the case with SLT. The LATTE system provides at least the advantage for patients with low pigmentation which often precludes precise visual identification of treatment targets.

As the LATTE system is performed in a supine patient, it could be performed on more patients than SLT. This is particularly relevant for obese patients, since sometimes SLT is very difficult for obese patients or patients with major neck or back issues preventing them from sitting at a chair.

The LATTE system does not require gonioscopy, which makes it significantly easier to use than TRAB360. In TRAB360, the surgeon has to perform gonioscopy, which includes challenges of blood on the cornea, blood in the anterior chamber, corneal striae and loss of viscoelastic coupling between the gonio lens to the cornea.

The LATTE system exhibits none of these previously mentioned challenges. The procedure involves the surgeon coupling the femtosecond laser with the patients eye, whereas in the LATTE system the laser is automatically guided to perform the treatment. This procedure exhibits similar success rates in the hands of a low volume comprehensive ophthalmologist similar to that of a high volume, highly-skilled glaucoma surgeon.

LATTE exhibits more convenience than SLT. With the reduced risk of an post-op intraocular pressure spike, there likely is no need for an intraocular check half an hour after the procedure, unlike with SLT. If the surgeon can use the LATTE system without corneal incisions, follow-up is less onerous than TRAB360, making LATTE more convenient. With the LATTE system, there is little preparation of the eye, and anesthesia is less. Therefore, this would facilitate workflow and efficiency of the LATTE system compared to conventional techniques.

Femtosecond laser-assisted cataract surgery has not demonstrated clear improvement over conventional phacoemulsification. However, femtosecond laser-assisted glaucoma surgery in the form we propose as the LATTE system has advantages over current manual glaucoma surgery techniques. For example, Dynamic OCT-A determines which glaucoma procedure is most appropriate for the patient. In addition, Dynamic OCT-A identifies Schlemm's canal more reliably than gonioscopy. Furthermore, automated laser-assisted transluminal trabecular excision treats the full 360 degrees of Schlemm's canal without incisional surgery. Finally, LATTE is potentially a repeatable procedure, whereas most MIGS are not repeatable.

While the exemplary embodiments focused on the identification of Schlemm's canal and the excision of portions of the trabecular meshwork, it would be understood by those skilled in the art, that the techniques presented herein applies to various parts of the eye that exhibit resistance to the aqueous flow, and to parts of the eye that exhibit other ocular issues that would require excision or any other form of laser treatment.

A number of implementations have been described. Nevertheless, it will be understood that various modifications may be made without departing from the spirit and scope of the invention.

The above-described embodiments are intended to be examples of the present invention and alterations and modifications may be effected thereto, by those of skill in the art, without departing from the scope of the invention, which is defined solely by the claims appended hereto.

The invention claimed is:

1. A system for diagnosing glaucoma, in a human eye, the system comprising:
   a coupling mechanism adapted for imparting pressure on an anterior region of said human eye; and
   an Optical Coherence Tomography Angiography (OCT-A) scanner producing three-dimensional imagery of regions of said human eye while said pressure is being imparted on said anterior region of said human eye by said coupling mechanism;
   wherein the coupling mechanism comprises a corneal portion and an episcleral portion;
   and wherein said corneal portion comprises at least one corneal central piston, and at least one corneal side piston.

2. The system of claim 1, wherein said episcleral portion comprises at least one piston.

3. The system of claim 1, further comprising a rotatable mirror for reflecting imagery for various portions of said human eye, into said OCT-A scanner.

4. The system of claim 1, further comprising one or more goniolenses formed on at least one of said corneal central piston and corneal side piston.

5. A system for treating glaucoma, in a human eye, the system comprising:
   the system of any one of claims 1 to 4; and
   a laser system for excising regions of said human eye based on said three-dimensional imagery.

6. The system of claim 5, further comprising a computer for processing imagery produced by said OCT-A scanner and identifying parts of said human eye.

7. The system of claim 6, further comprising a controller for directing said laser system to said regions of said human eye.

8. The system of claim 5, further comprising a controller for directing said laser system to said regions of said human eye.

9. A system for diagnosing glaucoma, in a human eye, the system comprising:
   a coupling mechanism adapted for imparting pressure on an anterior region of said human eye; and
   an Optical Coherence Tomography Angiography (OCT-A) scanner producing three-dimensional imagery of regions of said human eye while said pressure is being imparted on said anterior region of said human eye by said coupling mechanism;
   wherein the coupling mechanism comprises a corneal portion and an episcleral portion;
   and wherein said corneal portion comprises at least one corneal central fluid jet, and at least one corneal side fluid jet, for imparting pressure or suction on a corneal central part and a corneal side part, respectively, of said anterior region of said human eye.

10. The system of claim 9, wherein said episcleral portion comprises at least one episcleral fluid jet, for imparting pressure or suction on a scleral part of said anterior region of said human eye.

11. The system of claim 10, further comprising a rotatable mirror for reflecting imagery for various portions of said human eye, into said OCT-A scanner.

12. The system of claim 10, further comprising one or more goniolenses formed on at least one of said corneal central piston and corneal side piston.

13. A method of identifying portions of a human eye of a patient, comprising:
   causing the patient's blood to rush towards the patient's head causing an elevation in the episcleral venous pressure;
   imparting varying pressure on one of: a central cornea, a side cornea, and a sclera of said human eye using a coupling mechanism; and
   monitoring imagery produced by an OCT-A scanner and observing the flow of red blood cells in and out of Schlemm's canal, for identifying the location of Schlemm's canal and the trabecular meshwork of said human eye.

14. The method of claim 13, wherein the step of causing the patient's blood to rush towards the patient's head comprises placing the patient on a bed with a reclining body portion such that the patient is in a supine position.

15. The method of claim 13, wherein the step of causing the patient's blood to rush towards the patient's head comprises inserting the patient's lower body in a pressurized garment for exerting pressure on the patient's lower body.

16. A method of treating glaucoma, in a human eye, comprising:
   imparting varying pressure on one of: a central cornea, a side cornea, and a sclera of said human eye using a coupling mechanism;
   monitoring imagery produced by an OCT-A scanner and observing aqueous flow along the aqueous pathway, for identifying areas of resistance to aqueous drainage; and
   excising at least a portion of said areas of resistance using a laser based on said monitoring, for producing a channel for proper drainage of aqueous humor from said human eye;
   wherein the coupling mechanism comprises a corneal portion and an episcleral portion;
   and wherein said corneal portion comprises at least one corneal central piston, and at least one corneal side piston.

17. The method of claim 16, wherein said areas of resistance comprise the trabecular meshwork.

18. The method of claim 17, further comprising identifying the location of Schlemm's canal by observing said aqueous flow through Schlemm's canal.

* * * * *